US010295446B2

(12) United States Patent
Liu et al.

(10) Patent No.: US 10,295,446 B2
(45) Date of Patent: May 21, 2019

(54) APPARATUS FOR FULL-AUTOMATIC, ULTRA-LOW PRESSURE, FRACTIONATION-FREE AND NON-DESTRUCTIVE EXTRACTION OF WATER

(71) Applicant: Beijing Lica United Technology Limited, Beijing (CN)

(72) Inventors: Yayong Liu, Beijing (CN); Youwu Xing, Beijing (CN); Xiangning Zhu, Beijing (CN); Xiaobo Li, Beijing (CN)

(73) Assignee: Beijing Lica United Technology Limited, Beijing (CN)

( * ) Notice: Subject to any disclaimer, the term of this patent is extended or adjusted under 35 U.S.C. 154(b) by 221 days.

(21) Appl. No.: 15/519,683

(22) PCT Filed: Oct. 16, 2014

(86) PCT No.: PCT/CN2014/000916
§ 371 (c)(1),
(2) Date: Jul. 25, 2017

(87) PCT Pub. No.: WO2016/058112
PCT Pub. Date: Apr. 21, 2016

(65) Prior Publication Data
US 2018/0045624 A1 Feb. 15, 2018

(51) Int. Cl.
*B01D 3/10* (2006.01)
*G01N 1/34* (2006.01)
*G01N 1/10* (2006.01)
*B01D 3/42* (2006.01)
(Continued)

(52) U.S. Cl.
CPC .............. *G01N 1/34* (2013.01); *B01D 3/10* (2013.01); *B01D 3/42* (2013.01); *B01D 5/006* (2013.01);
(Continued)

(58) Field of Classification Search
CPC ... B01D 3/10; B01D 3/42; G01N 1/31; G01N 1/34; G01N 1/4022; G01N 1/42
See application file for complete search history.

(56) References Cited

U.S. PATENT DOCUMENTS 5,340,460 A * 8/1994 Kobayashi ............ C23C 14/564
156/345.27
8,061,056 B2 * 11/2011 Hedberg .................. B01D 1/14
118/320

(Continued)

FOREIGN PATENT DOCUMENTS

CN 102012327 A 4/2011
CN 102226632 A 10/2011
(Continued)

OTHER PUBLICATIONS

English language abstract for CN 102012327 A (2011).
(Continued)

*Primary Examiner* — Jonathan Miller
(74) *Attorney, Agent, or Firm* — Caesar Rivise, PC

(57) ABSTRACT

The invention provides a device for full-automatic, ultra-low pressure, fractionation-free and non-destructive extraction of water, including a control box, an extraction part, an ultra-low temperature cold trap and a transmission device, wherein the control box and the extraction part are located at the top of a cabinet, the ultra-low temperature cold trap is located inside the cabinet, a touch screen is arranged on the control box, a temperature control meter is arranged on a side face of the control box, the extraction part includes an upper layer plate, a middle layer plate, a bottom plate and a test tube, the bottom plate is fixedly installed on the cabinet, the test tube is accommodated in the ultra-low temperature cold trap, and the transmission device is fixedly installed on the bottom plate. The invention has the beneficial effects of being able to extract a plurality of samples at the same time, (Continued)

so the extraction efficiency is high; and no liquid nitrogen or organic solvent is required, thereby reducing the environmental pollution.

9 Claims, 5 Drawing Sheets

(51) Int. Cl.
  *B01D 5/00* (2006.01)
  *G01N 1/40* (2006.01)
  *G01N 1/42* (2006.01)

(52) U.S. Cl.
  CPC ............. *G01N 1/10* (2013.01); *G01N 1/4022* (2013.01); *G01N 1/42* (2013.01); *G01N 2001/4033* (2013.01)

(56) References Cited

U.S. PATENT DOCUMENTS

| | | | | |
|---|---|---|---|---|
| 8,679,307 | B2 * | 3/2014 | Fischione | G01N 1/32 118/719 |
| 2008/0022786 | A1 | 1/2008 | Sann et al. | |
| 2009/0165326 | A1 * | 7/2009 | Hedberg | B01D 1/14 34/312 |
| 2009/0249801 | A1 * | 10/2009 | Hedberg | B01D 5/0003 62/55.5 |
| 2011/0229928 | A1 * | 9/2011 | Dorward | G01N 1/42 435/29 |

FOREIGN PATENT DOCUMENTS

| | | |
|---|---|---|
| CN | 202853951 U | 4/2013 |
| CN | 103439164 A | 12/2013 |

OTHER PUBLICATIONS

English language abstract for CN 102226632 A (2011).
English language abstract for CN 103439164 A (2013).
English language abstract for CN 202853951 U (2013).
International Search Report for PCT/CN2014/000916 dated May 28, 2015.

* cited by examiner

US 10,295,446 B2

APPARATUS FOR FULL-AUTOMATIC, ULTRA-LOW PRESSURE, FRACTIONATION-FREE AND NON-DESTRUCTIVE EXTRACTION OF WATER

CROSS-REFERENCE TO RELATED APPLICATIONS

This application is the U.S. National Phase Application of PCT/CN2014/000916, filed Oct. 16, 2014, the content of which application is incorporated herein by reference in its entirety for all purposes.

FIELD OF THE INVENTION

The present invention relates to the field of experimental detection devices, and in particular to a device for full-automatic, ultra-low pressure, fractionation-free and non-destructive extraction of water.

BACKGROUND

With the deepening of ecological researches and environmental researches, the extraction and collection of plant water and soil water have been paid much attention by research institutions such as agriculture, forestry and environmental research institutes, however a perfect method for extracting the plant water and soil water has not been found yet, some of the existing technical methods require the use of liquid nitrogen cooling, while some employs toluene or xylene or the like as a solvent. In the traditional extraction methods, poisonous, harmful and expensive organic chemical reagents are used as solvents, which not only endangers the human health and the surrounding environment, and such used solvents are difficult to recycle, and this also has been the main reason of the high cost of plant extraction.

On the other hand, some people adopt the liquid nitrogen cooling mode, and liquid nitrogen needs to be manually added in the operation process, thereby the mode is cumbersome in operation, prone to nitrogen leakage and low in automation degree.

At present, although there are many water extraction methods, no corresponding matching product is available, the majority of laboratories assemble the products by using simple methods, so that the operation of the equipment is not reliable, and safety is relatively low. In a water extraction process, the extraction time of different types of samples are not the same, the used temperatures are different, but no one has done relevant research. The majority of samples for water extraction are collected from the field, the sample amount is limited, water separation failure is often caused by air leakage of connection, and accordingly the samples cannot be used again. As the sample amount is relatively large, the manual operation efficiency is low.

Therefore, the existing plant water and soil water extraction equipment and methods have obviously inconvenience and defects on structures and use, and need to be further improved urgently. In order to solve the problems, relevant manufacturers work hard to seek solutions, but no applicable design has been completed all the time, and general products have no suitable structure to solve the above problems, which is apparently the problem to be solved by relevant manufacturers urgently.

SUMMARY OF THE INVENTION

The objective of the present invention is to overcome the defects of the traditional extraction technology and provide a device for full-automatic, ultra-low pressure, fractionation-free and non-destructive extraction of water, in order to fundamentally solve the problems of difficulty in extraction and collection of plant water and soil water, low automation degree and incapability of simultaneous collection and separation of a plurality of samples.

The objective of the present invention is realized by adopting the following technical solution. The present invention provides a device for full-automatic, ultra-low pressure, fractionation-free and non-destructive extraction of water, including a control box, an extraction part, an ultra-low temperature cold trap and a transmission device, wherein the control box and the extraction part are located at the top of a cabinet, the ultra-low temperature cold trap is located inside the cabinet, a touch screen is arranged on the control box, a temperature control meter is arranged on a side face of the control box, the extraction part includes an upper layer plate, a middle layer plate, a bottom plate and a test tube, the bottom plate is fixedly installed on the cabinet, the test tube is accommodated in the ultra-low temperature cold trap, and the transmission device is fixedly installed on the bottom plate.

The objective of the present invention can also be further realized by adopting the following technical measures.

Preferably, according to the foregoing device for full-automatic, ultra-low pressure, fractionation-free and non-destructive extraction of water, the control box internally includes a main control board, a vacuum gauge tube, a vacuum pump and a temperature control meter, wherein the vacuum gauge tube is connected with one end of a KF flange tee, the other end of the KF flange tee is connected with an electromagnetic baffle valve, one end of the KF flange tee is connected with an air circuit in which electromagnetic valve seats are connected in parallel, and the electromagnetic baffle valve is connected with an air inlet of the vacuum pump.

Preferably, according to the foregoing device for full-automatic, ultra-low pressure, fractionation-free and non-destructive extraction of water, an air outlet of the vacuum pump is connected with the outside through a muffler.

Preferably, according to the foregoing device for full-automatic, ultra-low pressure, fractionation-free and non-destructive extraction of water, the transmission device includes a cross arm bearing and an air spring.

Preferably, according to the foregoing device for full-automatic, ultra-low pressure, fractionation-free and non-destructive extraction of water, the upper layer plate is fixed to a cross arm, and a rotating shaft on the upper layer plate can rotate around a bearing on the cross arm.

Preferably, according to the foregoing device for full-automatic, ultra-low pressure, fractionation-free and non-destructive extraction of water, a middle layer plate handle is fixed to the middle layer plate, one end of the air spring is fixed to the bottom plate, and the other end of the air spring is fixed to the cross arm.

Preferably, according to the foregoing device for full-automatic, ultra-low pressure, fractionation-free and non-destructive extraction of water, the upper layer plate is made of an aluminum material, a layer of heat conducting iron plate is laminated on the upper layer plate, a thermal baffle is arranged on the heat conducting iron plate, and an induction cooker is arranged on the thermal baffle.

Preferably, according to the foregoing device for full-automatic, ultra-low pressure, fractionation-free and non-destructive extraction of water, a locating pin is arranged on the upper layer plate, and the locating pin enters a locating branch angle after rotating and dropping with the cross arm.

Preferably, according to the foregoing device for full-automatic, ultra-low pressure, fractionation-free and non-destructive extraction of water, a locating block used for locating the middle layer plate is arranged on the bottom plate, the locating block and the electromagnetic valve seat are fixed to a carrier plate, thermal insulation cotton is arranged at the lower part of the bottom plate, an eccentric pressing device is arranged on the outer side of the bottom plate, and the eccentric pressing device is matched with the transverse arm for tight pressing.

Preferably, according to the foregoing device for full-automatic, ultra-low pressure, fractionation-free and non-destructive extraction of water, the locating block and the electromagnetic valve seat are fixed to the carrier plate, a two-way electromagnetic valve is fixed to the electromagnetic valve seat, a baffle plate is arranged on the carrier plate, and the test tube is fixed to an extraction block through a silica gel sealing tube.

Preferably, according to the foregoing device for full-automatic, ultra-low pressure, fractionation-free and non-destructive extraction of water, the electromagnetic valve seat includes an O-shaped ring groove, an O-shaped ring is placed in the O-shaped ring groove, the O-shaped ring groove is connected with a first air hole through a second air hole, the first air hole and the second air hole communicate with a third air hole, the third air hole is connected with one port of the two-way electromagnetic valve, another port of the two-way electromagnetic valve is connected with the third air hole, the third air hole is connected with a through hole, one end of the through hole is sealed, while the other end of the through hole is connected with one port of the KF flange tee after being connected with the through hole on the electromagnetic valve seat in parallel.

Preferably, according to the foregoing device for full-automatic, ultra-low pressure, fractionation-free and non-destructive extraction of water, an O-shaped ring groove is formed in a top end of the extraction block, an eighth air hole is formed in the middle of the O-shaped ring groove, a lower end of the eighth air hole stretches into the test tube, the test tube is sealed with the extraction block through a silica gel tube, a fifth air hole is formed in the side face of the eighth air hole, a Teflon tube is inserted into the fifth air hole, the Teflon tube is inserted into the bottom of the test tube, and the fifth air hole communicates with a sixth air hole and a process hole.

Preferably, according to the foregoing device for full-automatic, ultra-low pressure, fractionation-free and non-destructive extraction of water, a rotating shaft is arranged on the upper layer plate, a temperature sensor hole is formed in a front end of the upper layer plate, and a locating pin is arranged at the positive front end of the upper layer plate.

Preferably, according to the foregoing device for full-automatic, ultra-low pressure, fractionation-free and non-destructive extraction of water, the middle layer plate is provided with a sample bottle accommodation cavity, an O-shaped ring groove is formed in the outer periphery of the sample bottle accommodation cavity, a sample bottle accommodation cavity matched with the middle layer plate is arranged on the upper layer plate, and a locating branch angle is arranged on the middle layer plate.

Preferably, according to the foregoing device for full-automatic, ultra-low pressure, fractionation-free and non-destructive extraction of water, the main control board is respectively connected with a touch screen, a buzzer and a temperature sensor.

By means of the above-mentioned technical solutions, the foregoing device for full-automatic, ultra-low pressure, fractionation-free and non-destructive extraction of water of the present invention at least has the following advantages and beneficial effects: the device has the beneficial effects of being able to extract a plurality of samples at the same time, so the extraction efficiency is high; no liquid nitrogen or organic solvent is required, thereby reducing the environmental pollution; the extraction process is fully automatically controlled, thereby liberating manpower; non-destructive extraction of water can be realized so as to prevent isotope fractionation and ensure the extraction effect; and the system is designed in an integrated manner, so that the structure is compact and reliable. An ultra-low pressure separation system for extracting plant water and soil water in which the separation pressure is further reduced and compressor refrigeration is both safe and is not destructive to plants and soil structures is provided. The present invention achieves the rapid separation of water under the optimum temperature and pressure, controls the heating and cooling, controls the vacuum degree, realizes fully automatic control and completely non-destructive extraction of water and prevents isotope fractionation. Moreover, the damage to sample structures is prevented by using novel low temperature technology. The system designs built-in parameters by researching the correlation among the temperature, the vacuum degree and the required time, and uses different temperatures, vacuum degrees and extraction time to achieve water separation according to different sample types.

The foregoing description is merely an overview of the technical solutions of the present invention and can be implemented in accordance with the contents of the description in order to enable a clearer understanding of the technical means of the present invention, to make the above-mentioned and other objectives, features and advantages of the present invention be more obvious, preferred embodiments are cited below in with reference to the accompanying drawings, which are described in detail below.

REFERENCE SIGNS

| | |
|---|---|
| 1: control box | 2: touch screen |
| 3: temperature control meter | 4: ultra-low temperature cold trap |
| 5: cabinet | 6: induction cooker |
| 7: cross arm | 8: cross arm support |

-continued

| | |
|---|---|
| 9: bottom plate | 10: heating block cover |
| 11: electromagnetic valve cover | 12: eccentric pressing device |
| 13: leakage protector | 14: socket with switch |
| 15: relay | 16: main control board |
| 17: KF flange tee | 18: vacuum gauge tube |
| 19: electromagnetic baffle valve | 20: vacuum pump |
| 21: AC-DC switching power supply | 22: temperature control meter |
| 23: air spring | 24: electromagnetic valve |
| 25: electromagnetic valve seat | 26: middle layer plate |
| 27: upper layer plate | 28: middle layer plate handle |
| 29: cross arm bearing | 30: test tube |
| 31: buzzer | 32: temperature sensor |
| 33: two-way electromagnetic valve | 34: relay |
| 35: vacuum pump | 36: bearing |
| 37: limit switch | 38: temperature switch |
| 39: temperature fuse | 40: extraction block |
| 41: locating block | 42: baffle plate |
| 43: thermal insulation cotton | 44: sample bottle |
| 45: locating branch angle | 46: thermal baffle |
| 47: seventh air hole | 48: O-shaped ring groove |
| 49: locating pin | 50: rotating shaft |
| 51: temperature sensor hole | 52: eighth air hole |
| 53: O-shaped ring groove | 54: fifth air hole |
| 55: sixth air hole | 56: process hole |
| 57: O-shaped ring groove | 58: first air hole |
| 59: second air hole | 60: third air hole |
| 61: fourth air hole | 62: through hole |
| 63: thermal baffle | 64: heat conducting iron plate |
| 65: carrier plate | 66: heating relay |
| 67: refrigeration relay | 68: electromagnetic valve relay |
| 69: extraction part | 70: transmission device |

DETAILED DESCRIPTION OF THE EMBODIMENTS

In order to further illustrate the technical means and efficacy of the present invention for achieving the intended objectives of the present invention, specific embodiments, structure, features and effects of a device for full-automatic, ultra-low pressure, fractionation-free and non-destructive extraction of water provided by the present invention are illustrated below in detail in combination with the accompanying drawings and preferred embodiments.

Figure 1:
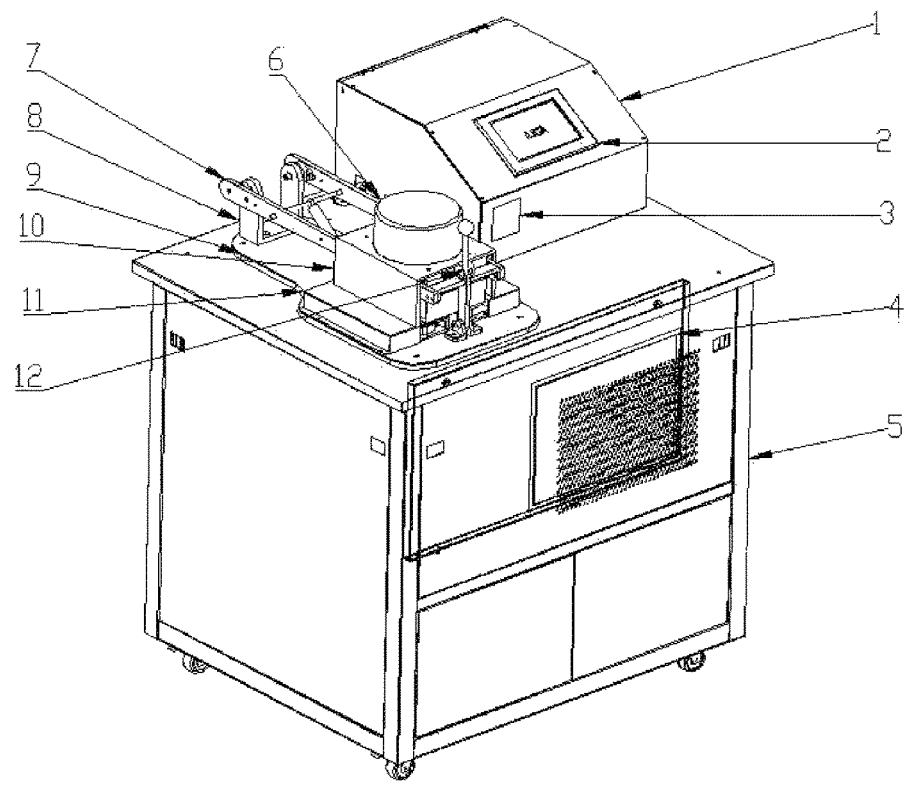
FIG. 1 is an overall structure diagram of the system.

As shown in FIG. 1, a control box 1 is installed on a cabinet 5 to automatically control an extraction system. A touch screen 2 is installed on the control box 1 for setting parameters and monitoring a collection process. A temperature control meter 3 can set a heating temperature range and displays a current temperature. An ultra-low temperature cold trap 4 is placed in the cabinet 5 for condensing the water vapor in a test tube 30 so as to collect water in a solid state. A bottom plate 9 is fixed on the cabinet 5, and an extraction part of the system is installed thereon. A cross arm support 8 is fixed to the bottom plate 9, a cross arm 7 is fixed by a cross arm bearing 29, and the cross arm 7 can rotate around the cross arm bearing. An induction cooker 6 heats a sample bottle 44 in a middle layer plate 26 to sublimate the water, and the water is condensed after entering the test tube 30. An electromagnetic valve cover 11 is fixed to the bottom plate 9 for protecting an electromagnetic valve 24 on an electromagnetic valve seat 25.

Figure 2:
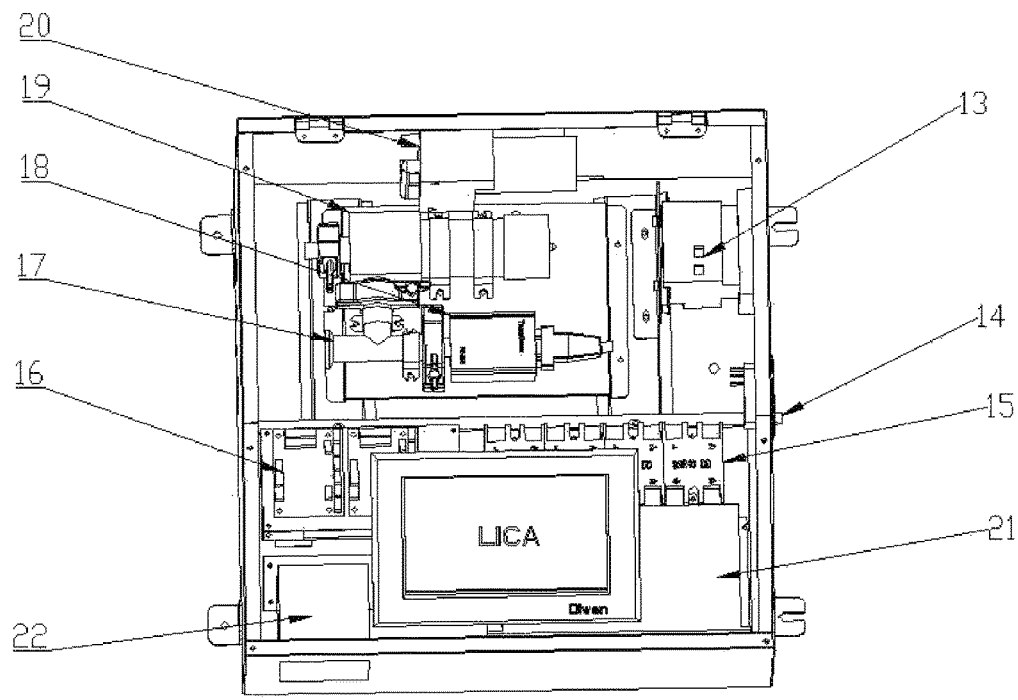
FIG. 2 is a partial structure diagram of a control box.

As shown in FIG. 2, a leakage protector 13, a socket 14 with a switch, a relay 15, a main control board 16, a KF flange tee 17, a vacuum gauge tube 18, an electromagnetic baffle valve 19, a vacuum pump 20, an AC-DC switching power supply 21 and a temperature control meter 22 are fixedly installed in the control box 1 for controlling the extraction system. One end of the KF flange tee 17 is connected with the vacuum gauge tube 18, the other end of the KF flange tee is connected with the electromagnetic baffle valve 19, the electromagnetic baffle valve 19 is connected with an air inlet of the vacuum pump 20, and an air outlet of the vacuum pump 20 is connected with the outside through a muffler. One end of the KF flange tee 17 is connected with an air circuit in which two electromagnetic valve seats 25 are connected in parallel, so that the vacuum pump 20 can perform a vacuumizing operation on each path.

Figure 3:
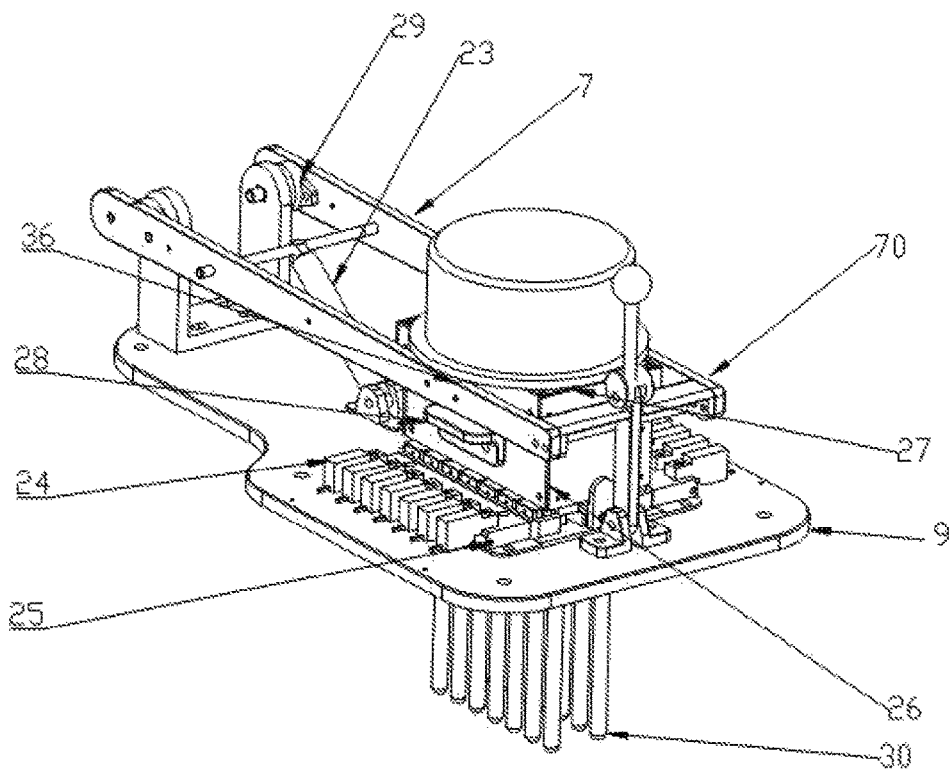
FIG. 3 is a schematic diagram of a connection structure of an extraction part and a transmission device.

As shown in FIG. 3, an upper layer plate 27 is fixed to the cross arm 7, a rotating shaft 50 on the upper layer plate 27 can rotate around a bearing 36 on the cross arm 7. A middle layer plate handle 28 is fixed to the middle layer plate 26 so as to facilitate the movement of the middle layer plate. One end of an air spring 23 is fixed to the bottom plate 9, and the other end of the air spring is fixed to the cross arm 7 through an optical axis, so that when the cross arm rotates around the bearing 36, damping is formed for realizing random parking between two opening and closing positions.

Figure 4:
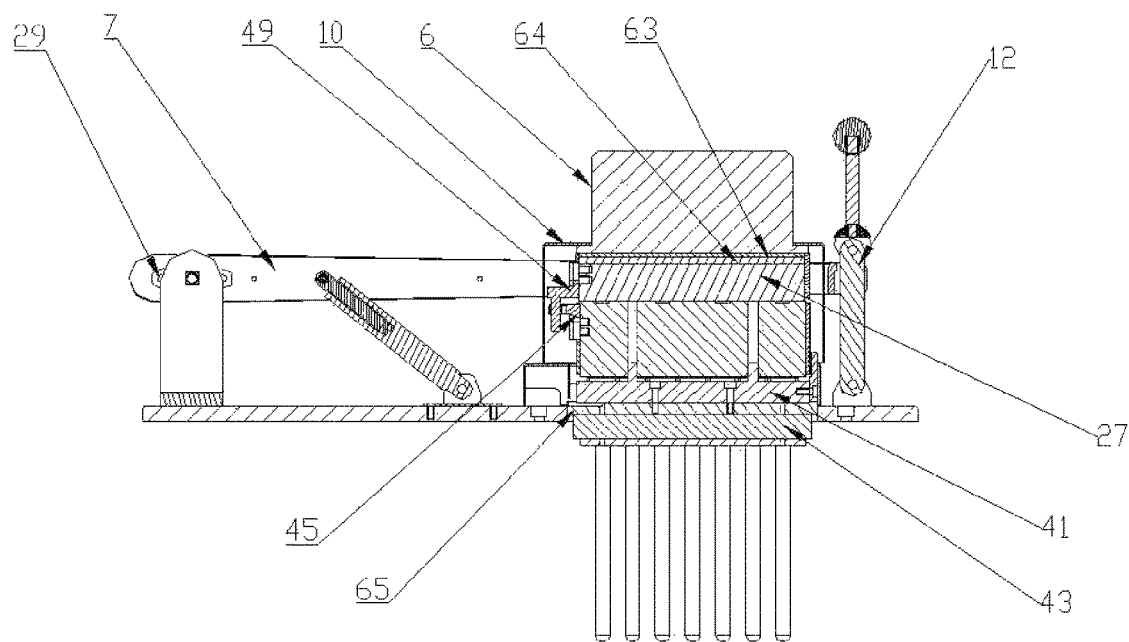
FIG. 4 is a sectional view of the connection structure of the extraction part and the transmission device.

As shown in FIG. 4, the upper layer plate 27 is made of an aluminum material, a layer of heat conducting iron plate 64 is laminated on the upper layer plate, a layer of thermal baffle 63 is laminated on the heat conducting iron plate 64, and the induction cooker 6 is laminated on the thermal baffle 63. The induction cooker 6 generates heat in the heat conducting iron plate 64 through internal coils after being energized, and the heat is transmitted to the aluminum upper layer plate 27. The thermal baffle 63 prevents the heat conducting iron plate 64 from conducting the heat upwards to transmit excessive heat to the induction cooker 6 to damage the induction cooker 6. A locating pin 49 on the upper layer plate 27 enters a locating branch angle 45 after rotating and dropping off with the cross arm 7 on the upper layer plate 27, so that the hole in the upper layer plate 27 can correspond to the hole in the middle layer plate 26 accurately. The middle layer plate 26 is carried away from or carried into the extraction part of the system by a middle layer plate handle 28. When the middle layer plate 26 is carried into the system, the hole in the bottom of the middle layer plate 26 is located by a pin inserted into a locating block 41. The locating block 41 and an electromagnetic valve seat 25 are fixed to a carrier plate 65, and the carrier plate 65 is fixed to the bottom plate 9. When the extraction part and the cabinet 5 are fixed, thermal insulation cotton 43 enters a pot type cold trap in the ultra-low temperature cold trap 4, and the thermal insulation cotton 43 isolates the low temperature in the cold trap from the high temperature above the carrier plate 65. When all of the 14 extraction blocks 40 are placed on the carrier plate 65, the middle layer plate 26 is also placed by the locating block 41, when the upper layer plate 27 rotates and drops onto the middle layer plate 26 with the cross arm 7, an eccentric pressing device 12 presses the cross brace on the cross arm 7, and the air circuit of the system is sealed by an internal O-shaped ring.

Figure 5:
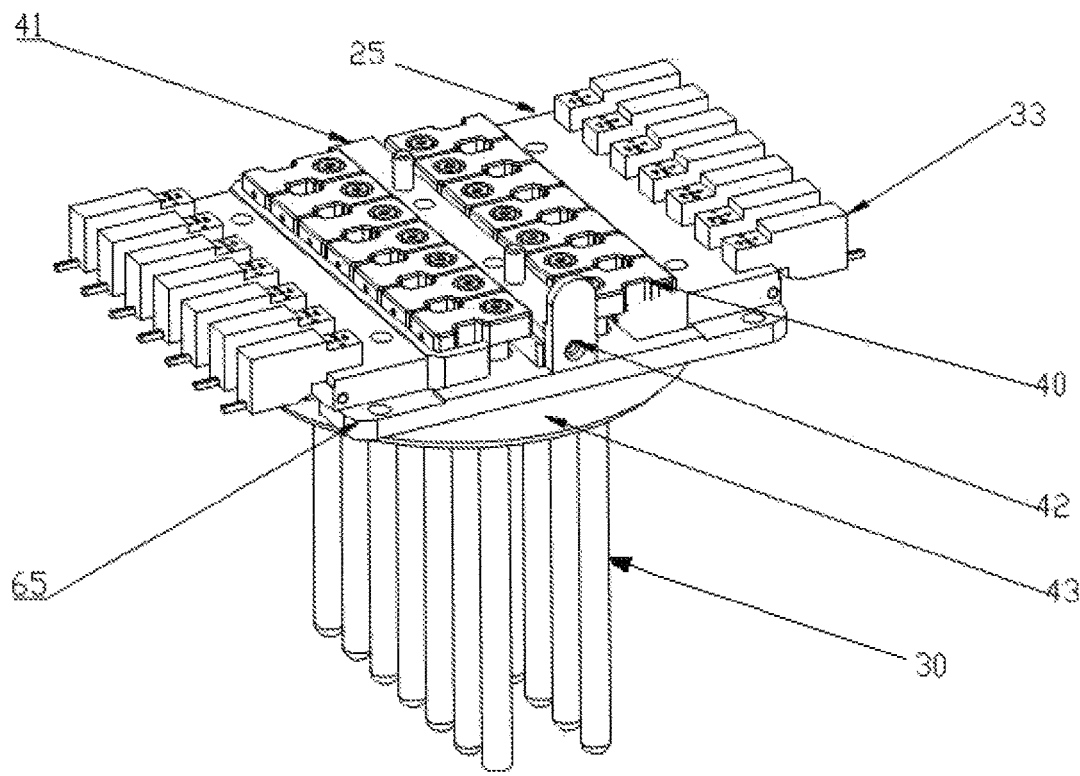
FIG. 5 is a partial structure diagram of a lower layer plate.

As shown in FIG. 5, the locating block 41 and the electromagnetic valve seat 25 are fixed to the carrier plate 65, a two-way electromagnetic valve 33 is fixed to the electromagnetic valve seat 25, and the 14 extraction blocks 40 are placed on the locating block 41 and the electromagnetic valve seat 25 and are located. When a baffle plate 42 drops from the middle layer plate 26, it plays a certain guide function. A test tube 30 is fixed to an extraction block 40 through a silica gel sealing tube.

Figure 6:
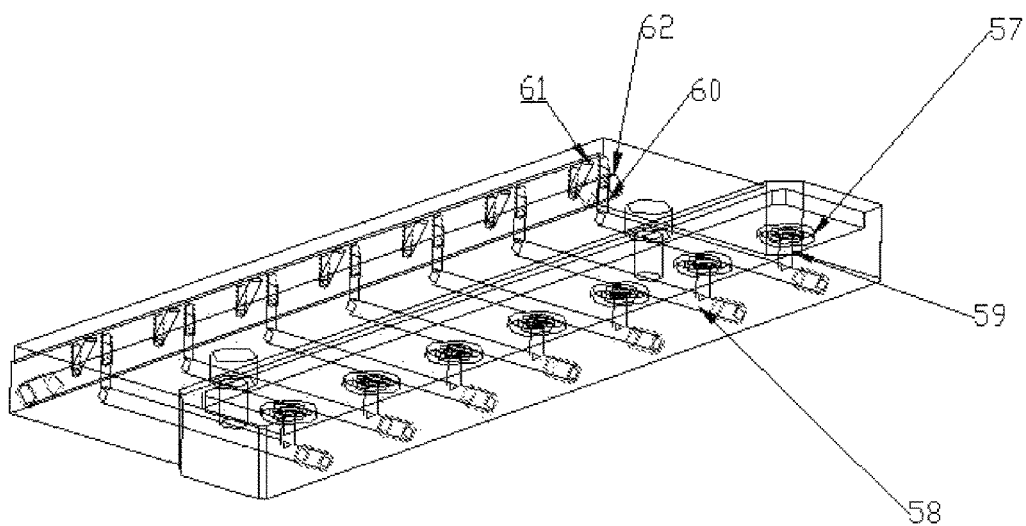
FIG. 6 is a structure diagram of an electromagnetic valve seat.

As shown in FIG. 6, an O-shaped ring is placed in an O-shaped ring groove 57 for sealing the lower end of the extraction block 40 with the electromagnetic valve seat 25. A second air hole 59 communicates with a first air hole 58 and a third air hole 60, the third air hole 60 is connected with one port of the two-way electromagnetic valve 33, another port of the two-way electromagnetic valve 33 is connected with a fourth air hole 61, the fourth air hole 61 is connected with a through hole 62, one end of the through hole 62 is sealed, and the other end of the through hole is connected with one port of the KF flange tee 17 after being connected with the through hole 62 on the electromagnetic valve seat 25 in parallel. The orifice of the first air hole 58 is sealed after being processed.

Figure 7:
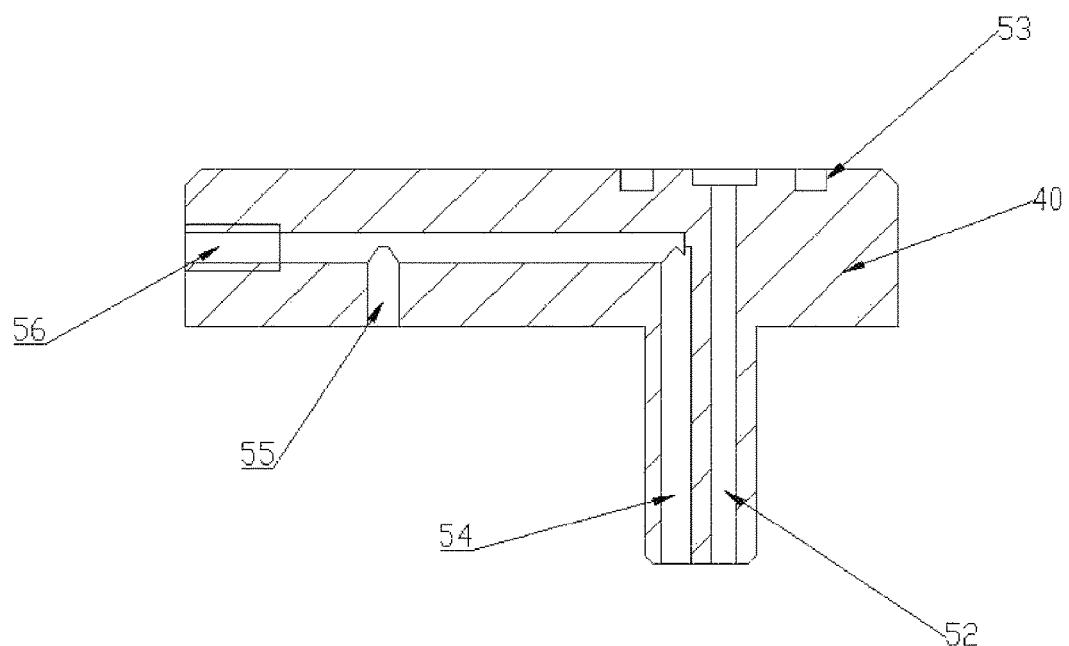
FIG. 7 is a structure diagram of the electromagnetic valve seat.

As shown in FIG. 7, an O-shaped ring is placed in an O-shaped ring groove 53 for sealing the upper end of the extraction block 40 with the middle layer plate 26. The upper end of an eighth air hole 52 is aligned to a seventh air hole 47 on the middle layer plate 26, and the seal during the butt joint of the two holes is sealed by the O-shaped ring groove 53. The lower end of the eighth air hole 52 stretches into the test tube 30, and the test tube 30 is sealed with the extraction block 40 through a silica gel tube. A Teflon tube is inserted into a fifth air hole 54, the Teflon tube is inserted into the bottom of the test tube 30, the fifth air hole 54 communicates with a sixth air hole 55 and a process hole 56, and the orifice of the process hole 56 is sealed after being processed. When the extraction block 40 is installed on the electromagnetic valve seat 25, the sixth air hole 55 communicates with the second air hole 59 on the electromagnetic valve seat 25, and the seal during the butt joint of the two holes is sealed by the O-shaped ring groove 57.

Figure 8:
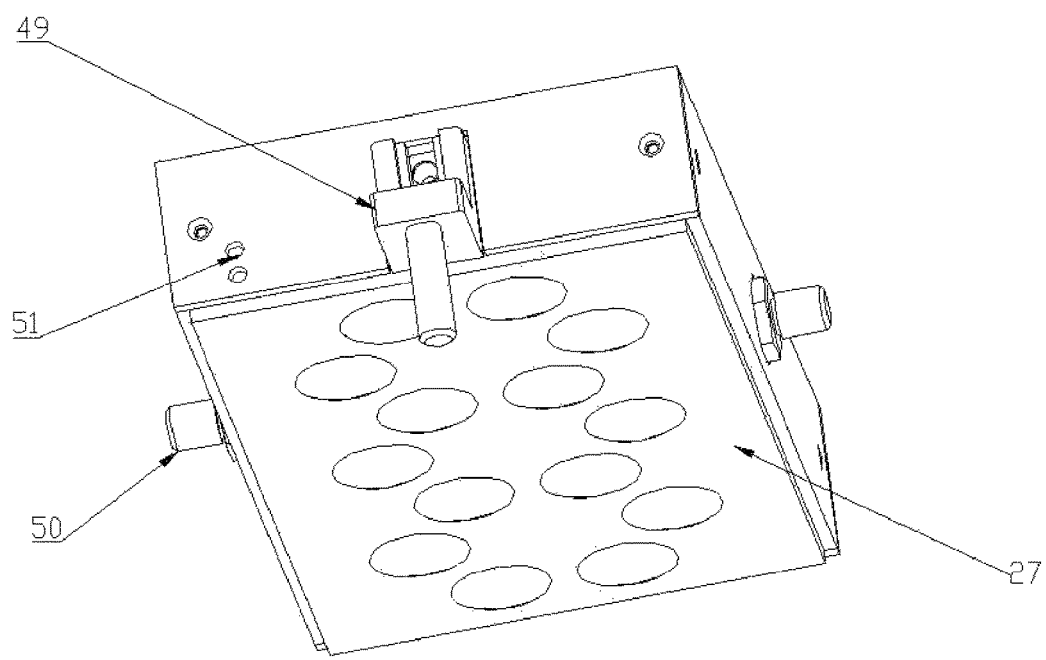
FIG. 8 is a partial structure diagram of an upper layer plate.

As shown in FIG. 8, the rotating shaft 50 is fixed to the upper layer plate 27, and the rotating shaft 50 can rotate around the bearing 36 on the cross arm 7. A temperature sensor is installed in a temperature sensor hole 51 for detecting the temperature of the upper layer plate. The locating pin 49 is fixed to the upper layer plate 27.

Figure 9A:
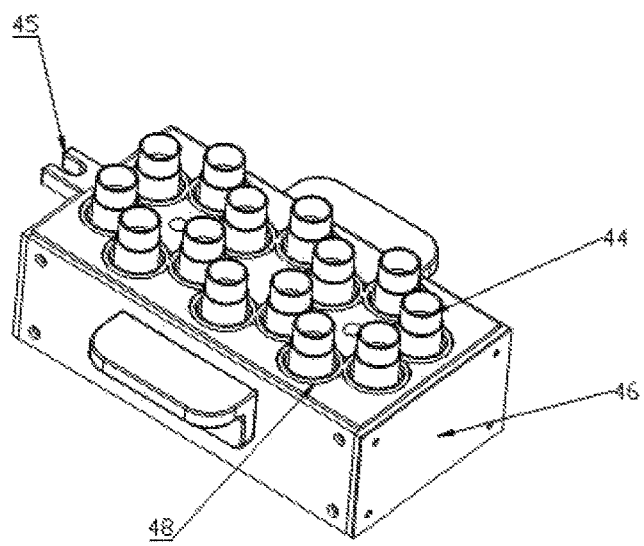
FIG. 9A is a partial structure diagram of a middle layer plate.
Figure 9B:
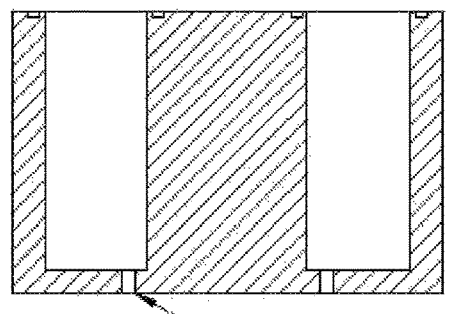
FIG. 9B is a sectional view of FIG. 9A.

As shown in FIG. 9A, prior to the extraction, the bottle cap of the sample bottle 44 is taken off and is put in the sample bottle accommodation cavity of the middle layer plate 26 firstly, and then the sample bottle 44 is put in the sample bottle accommodation cavity as well. An O-shaped ring is placed in an O-shaped ring groove 48 for sealing the upper end face of the middle layer plate 26 with the lower end face of the upper layer plate 27. A thermal baffle 46 prevents the heat loss of the middle layer plate 26. A locating branch angle 45 is fixed to the middle layer plate.

Figure 10:
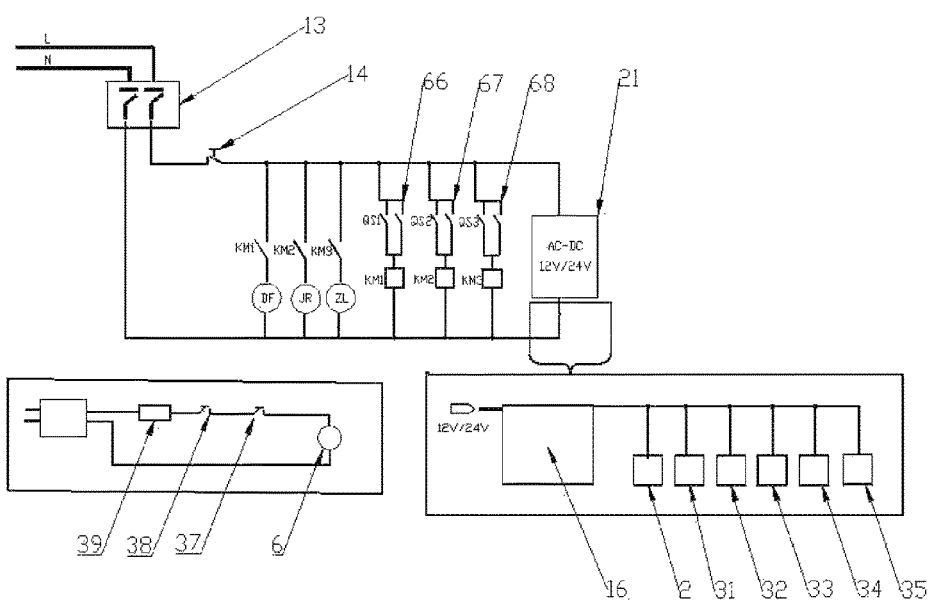
FIG. 10 is a functional block diagram of a system circuit.

As shown in FIG. 10, 220V AC enters the leakage protector 13 and provides power supply for the entire control system through the socket 14 with the switch, the 220V AC is converted into two paths of 24V DC and 12V DC by the AC-DC switching power supply 21, which are respectively supplied to the 12V main control board 16; the main control board 16 respectively controls a heating relay 66, a refrigeration relay 67 and an electromagnetic valve relay 68; the heating is realized by the induction cooker 6, the heating part has overcurrent protection and overheat protection functions, and performs safety protection through a temperature fuse 39, a temperature switch 38 and a limit switch 37; and the main control board controls a measurement part, is provided with an LCD touch screen 2 for displaying measurement data and system state, a buzzer 31 having the functions of prompting alarm and alarming, a temperature sensor 32, the two-way electromagnetic valve 33, an electromagnetic valve 24 for controlling the air circuit and a vacuum pump 35 for vacuumizing.

The present invention adopts the principle of ultra-low pressure vacuum distillation and refrigeration, fractionation-free and non-destructive refrigeration collection of water is realized by using the technology of evaporating or sublimating water in an ultra-low pressure environment and condensing water in a low temperature environment, and all the water in the sample is extracted without fractionation. The system is mainly composed of an ultra-low pressure system, a heating system, a refrigeration system and a collection control system. The ultra-low pressure system mainly maintains a specific vacuum degree for the refrigeration system, the heating system and a pipeline so as to facilitate fastest movement of water. The heating system heats the sample to evaporate water, the evaporated water enters the refrigeration system under the action of gradient caused by the ultra-low pressure to be frozen to ice. The entire process is automatically completed under the intervention of the collection control system.

When the instrument works, each sample is used as an independent channel, and the vacuum pump is firstly opened to reduce the pressure of each channel to a low pressure of lower than 500 Pa. The water vapor moves into a condensation tube to be frozen under the action of the pressure gradient and is sealed in a water vapor separation tube; and then the sample is heated to separate and freeze the residual water in the sample by using a low temperature freezing method, and thus the water in the sample is completely separated and frozen (higher than 99%).

1) The ultra-low pressure system is mainly composed of a vacuum pump, a vacuum electromagnetic baffle valve, a vacuum gauge tube, a multipath vacuum electromagnetic valve and a control module, the vacuum pump is the power for maintaining the ultra-low pressure of the entire system, the vacuum pressure of each channel is detected by the vacuum gauge tube, and the control module respectively controls respective vacuum electromagnetic valves and the total valve, namely the vacuum electromagnetic baffle valve and adjusts the vacuum degree of the system, so as to realize the optimal water movement condition.

2) The heating system is mainly composed of a temperature controller, an induction cooker, a heat conducting iron plate and a temperature sensor. The sample is connected to the vacuum system and is placed in a heating accommodation cavity, and the heating system controls the water in the sample to evaporate to form the necessary temperature. The release of other organic volatile matters in the sample can be inhibited by temperature control so as to keep the cleanness of the extracted water. The present invention adopts an electromagnetic heating mode, so the heating efficiency is quite high.

3) The refrigeration system is composed of a heat preservation box body, a compressor, a condenser, an evaporator, a drying filter and a capillary tube. The compressor provides the power of the refrigeration cycle system, can drive a refrigerant to circulate back and forth in the pipeline of the system and achieves a refrigeration function by thermal power conversion. The condenser can also be called a radiator and functions as converting the high-temperature and high-pressure refrigerant and overheated vapor discharged from the compressor into medium-temperature and high-pressure supercooled liquid through external heat exchange, and the heat is transmitted to the outside by the condenser. The evaporator is also called a cooler, when the liquid refrigerant is vaporized and evaporated in the evaporator, it absorbs the heat in the heat preservation box body and cools the heat preservation box so as to achieve the refrigeration objective. A collection tube is located in the refrigeration system and can collect the transferred vaporous water in a solid state.

4) The collection control system is composed of a singlechip-cored data processing system and monitors and controls the entire system. A human-computer interaction interface is convenient for a user to set parameters, observe the pressure, temperature and other data of the system in real time, and control the system.

Although the present invention has been illustrated and described with reference to certain specific embodiments above, it is not intended that the present invention is limited to various details therein. On the contrary, various modifications may be made on various details without departing from the spirit of the present invention, within the category and scope of equivalency of the claims. Therefore, other parts are not described in detail.

The foregoing descriptions are merely preferred embodiments of the present invention and are not limitations to the present invention in any form. Although the present invention have been disclosed above by the preferred embodiments, the present invention is not limited thereto, anyone who is familiar with this art can make some alterations or modifications by use of the technical contents disclosed above to serve as equivalent embodiments of equivalent variations without departing from the scope of the technical solutions of the present invention, and any simple modifications, equivalent variations and modifications made to the above embodiments according to the technical essence of the present invention without departing from the contents of the technical solutions of the present invention still fall within the scope of the technical solutions of the present invention.

The invention claimed is:

1. A device for full-automatic, ultra-low pressure, fractionation-free and non-destructive extraction of water, comprising:
a control box, which internally comprises a main control board, a vacuum gauge tube, a vacuum pump, and a temperature control meter, wherein the vacuum gauge tube is connected with a first end of a KF flange tee, a second end of the KF flange tee is connected with an electromagnetic baffle valve, a third end of the KF flange tee is connected with an air circuit in which electromagnetic valve seats are connected in parallel, and the electromagnetic baffle valve is connected with an air inlet of the vacuum pump,
an extraction part,
an ultra-low temperature cold trap and
a transmission device,
wherein the control box and the extraction part are located at a top of a cabinet, the ultra-low temperature cold trap is located inside the cabinet, a touch screen is arranged on the control box, a temperature control meter is arranged on a side face of the control box, the extraction part comprises an upper layer plate, a middle layer plate, a bottom plate and a test tube, the bottom plate is fixedly installed on the cabinet, the test tube is accommodated in the ultra-low temperature cold trap, and the transmission device is fixedly installed on the bottom plate.

2. The device for full-automatic, ultra-low pressure, fractionation-free and non-destructive extraction of water of claim 1, wherein an air outlet of the vacuum pump is connected with the outside through a muffler.

3. The device for full-automatic, ultra-low pressure, fractionation-free and non-destructive extraction of water of claim 1 or 2, wherein the transmission device comprises a cross arm bearing and an air spring.

4. The device for full-automatic, ultra-low pressure, fractionation-free and non-destructive extraction of water of claim 1 or 2, wherein the upper layer plate is fixed to a cross arm, and a rotating shaft on the upper layer plate can rotate around a bearing on the cross arm.

5. The device for full-automatic, ultra-low pressure, fractionation-free and non-destructive extraction of water of claim 1 or 2, wherein a middle layer plate handle is fixed to the middle layer plate, one end of the air spring is fixed to the bottom plate, and the other end of the air spring is fixed to the cross arm.

6. The device for full-automatic, ultra-low pressure, fractionation-free and non-destructive extraction of water of claim 1 or 2, wherein the upper layer plate is made of an aluminum material, a layer of heat conducting iron plate is laminated on the upper layer plate, a thermal baffle is arranged on the heat conducting iron plate, and an induction cooker is arranged on the thermal baffle.

7. The device for full-automatic, ultra-low pressure, fractionation-free and non-destructive extraction of water of claim 6, wherein a locating pin is arranged on the upper layer plate, and the locating pin enters a locating branch angle after rotating and dropping off with the cross arm.

8. The device for full-automatic, ultra-low pressure, fractionation-free and non-destructive extraction of water of claim 1 or 2, wherein a locating block used for locating the middle layer plate is arranged on the bottom plate, the locating block and the electromagnetic valve seats are fixed to a carrier plate, thermal insulation cotton is arranged at the lower part of the bottom plate, an eccentric pressing device is arranged on the outer side of the bottom plate, and the eccentric pressing device is matched with the transverse arm for tight pressing.

9. The device for full-automatic, ultra-low pressure, fractionation-free and non-destructive extraction of water of claim 8, wherein the locating block and the electromagnetic valve seats are fixed to the carrier plate, a two-way electromagnetic valve is fixed to the electromagnetic valve seats, a baffle plate is arranged on the carrier plate, and the test tube is fixed to an extraction block through a silica gel sealing tube.

* * * * *